(12) United States Patent
Faria et al.

(10) Patent No.: US 11,406,474 B2
(45) Date of Patent: Aug. 9, 2022

(54) EQUIPMENT CLIP FOR UROLOGY AND METHODS FOR USE

(71) Applicant: KPR U.S., LLC, Mansfield, MA (US)

(72) Inventors: Kolby Austin Faria, Riverside, RI (US); Steven Bradford Cote, Mendon, MA (US); Taylor Kathleen Rohan, Allston, MA (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

(21) Appl. No.: 17/025,946

(22) Filed: Sep. 18, 2020

(65) Prior Publication Data

US 2021/0085426 A1    Mar. 25, 2021

Related U.S. Application Data

(60) Provisional application No. 62/902,494, filed on Sep. 19, 2019.

(51) Int. Cl.
*A61B 90/57* (2016.01)
*A61M 5/14* (2006.01)
*A61B 50/20* (2016.01)

(52) U.S. Cl.
CPC .......... *A61B 90/57* (2016.02); *A61M 5/1418* (2013.01); *A61B 50/20* (2016.02)

(58) Field of Classification Search
CPC .... A61M 5/1416; A61B 50/20; Y10T 24/344; Y10T 24/3444; Y10T 24/3433; Y10T 24/3431
See application file for complete search history.

(56) References Cited

U.S. PATENT DOCUMENTS

| 2,433,171 | A | | 12/1947 | Tegarty | |
| 4,835,824 | A | | 6/1989 | Durham et al. | |
| 5,159,731 | A | * | 11/1992 | Dereadt | D06F 55/00 24/552 |
| 9,919,125 | B2 | * | 3/2018 | Gulliver | A61M 16/0875 |
| 10,195,387 | B2 | | 2/2019 | Gulliver et al. | |
| 10,285,768 | B2 | | 5/2019 | O'Brien | |
| 2013/0061857 | A1 | * | 3/2013 | McNally | A61B 50/20 128/852 |

* cited by examiner

*Primary Examiner* — Robert Sandy
(74) *Attorney, Agent, or Firm* — ArentFox Schiff LLP (57) ABSTRACT

The present disclosure provides a device for holding at least one conduit. The device includes a ring having a first end and a second end. The device also includes a first clamping jaw extending from the first end of the ring. The device also includes a second clamping jaw extending from the first end of the ring. A first clamping surface of the first jaw contacts a second clamping surface of the second jaw in a first position, and the first clamping surface is spaced apart from the second clamping surface in a second position. The device transitions from the first position to the second position in response to application of an external force applied to an exterior surface of the ring between the first end and the second end. The device also includes a channel including an inlet positioned at the second end of the ring. The channel is configured to releasably receive the at least one conduit via the inlet, and the channel prevents the at least one conduit from contacting the first end of the ring.

20 Claims, 5 Drawing Sheets

EQUIPMENT CLIP FOR UROLOGY AND METHODS FOR USE

FIELD OF THE INVENTION

The present disclosure relates to devices for holding at least one conduit in a repositionable and secure manner. In particular, the present disclosure relates to a conduit management device for use in a hospital or other medical setting, the device including clamping jaws to secure the device to a sheet material associated with the bed or patient.

BACKGROUND

Unless otherwise indicated herein, the materials described in this section are not admitted to be prior art to the claims in this application.

In the medical field, it is often necessary to clamp a variety of conduits to a stationary surface when the conduits are m use. Such conduits can include feeding tubes, electrical cords, urology tubes, nasogastric tubes, chest tubes, catheter tubes, dialysis tubes, ventilator circuit tubing, other conduits for introducing fluids intravenously or through the nose or mouth of the patient, and/or other conduits for removing fluids from the patient.

One problem with use of these types of conduits is interference with medical procedures or interference with general patient movement. Another problem is ease of use to secure and operate a clip for insertion and removal of conduits therein.

SUMMARY

In view of the foregoing, the present disclosure relates to an improved combined sheet clip and conduit management device that provides improved grip strength and ease of operation while reducing the amount of material required to manufacture the clip.

Thus, in a first aspect, a device for holding at least one conduit is provided. The device includes a ring having a first end and a second end. The device also includes a first clamping jaw extending from the first end of the ring, wherein the first clamping jaw includes a first clamping surface. The device also includes a second clamping jaw extending from the first end of the ring, wherein the second clamping jaw includes a second clamping surface, the first clamping surface contacts the second clamping surface in a first position, the first clamping surface is spaced apart from the second clamping surface in a second position, and the device transitions from the first position to the second position in response to application of an external force applied to an exterior surface of the ring between the first end and the second end. The device also includes a channel including an inlet positioned at the second end of the ring, wherein the channel is configured to releasably receive the at least one conduit via the inlet, and the channel prevents the at least one conduit from contacting the first end of the ring.

In a second aspect, a method for holding at least one conduit is provided. The method includes applying an external force to an exterior surface of a ring of the device (the ring of the device being a ring as described in accordance with the first aspect) between the first end and the second end of the ring, thereby increasing a distance between the first clamping surface and the second clamping surface. The method also includes positioning a portion of a sheet material between the first clamping surface and the second clamping surface of the ring. The method further includes positioning a conduit into the device channel through the inlet. The method also includes removing the external force from the exterior surface of the ring, thereby decreasing the distance between the first clamping surface and the second clamping surface such that the sheet material is secured between the first clamping surface and the second clamping surface.

These as well as other aspects, advantages, and alternatives, will become apparent to those of ordinary skill in the art by reading the following detailed description, with reference where appropriate to the accompanying drawings.

DETAILED DESCRIPTION

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements and dimensions, unless otherwise specified, "about" and "substantially" each means +/−5% of a stated value. Individual measurements or dimensions may vary within this range without altering the fundamental nature of the scope and function of the devices and methods disclosed herein. However, as the ordinarily skilled artisan will appreciate, measurements and dimensions outside of this range may also provide the desired function without altering the fundamental nature of the devices and methods disclosed herein.

As used herein, "conduit" means any tubing or conduit comprising a long object (usually cylindrical) used to hold and/or conduct objects, liquids, gases, electrical current, cabling, or to transmit data appropriate for use in the medical field. For example, a "conduit" can comprise electrical cords, medical tubing, feeding tubes, urology tubes, nasogastric tubes, chest tubes, catheter tubes, dialysis tubes, ventilator circuit tubing, and other conduits for introducing fluids intravenously, through the nose or mouth of the patient, or removing fluids from the patient.

As used herein, "coupled" means associated directly as well as indirectly. For example, a member A may be directly associated with a member B, or may be indirectly associated therewith, e.g., via another member C.

In the following description, numerous specific details are set forth to provide a thorough understanding of the disclosed concepts, which may be practiced without some or all of these particulars. In other instances, details of known devices and/or processes have been omitted to avoid unnecessarily complicating and obscuring the disclosure. While some concepts will be described in conjunction with specific examples, it will be understood that these examples are not intended to be limiting.

Unless otherwise indicated, the terms "first," "second," etc. are used herein merely as labels and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Figure 1:
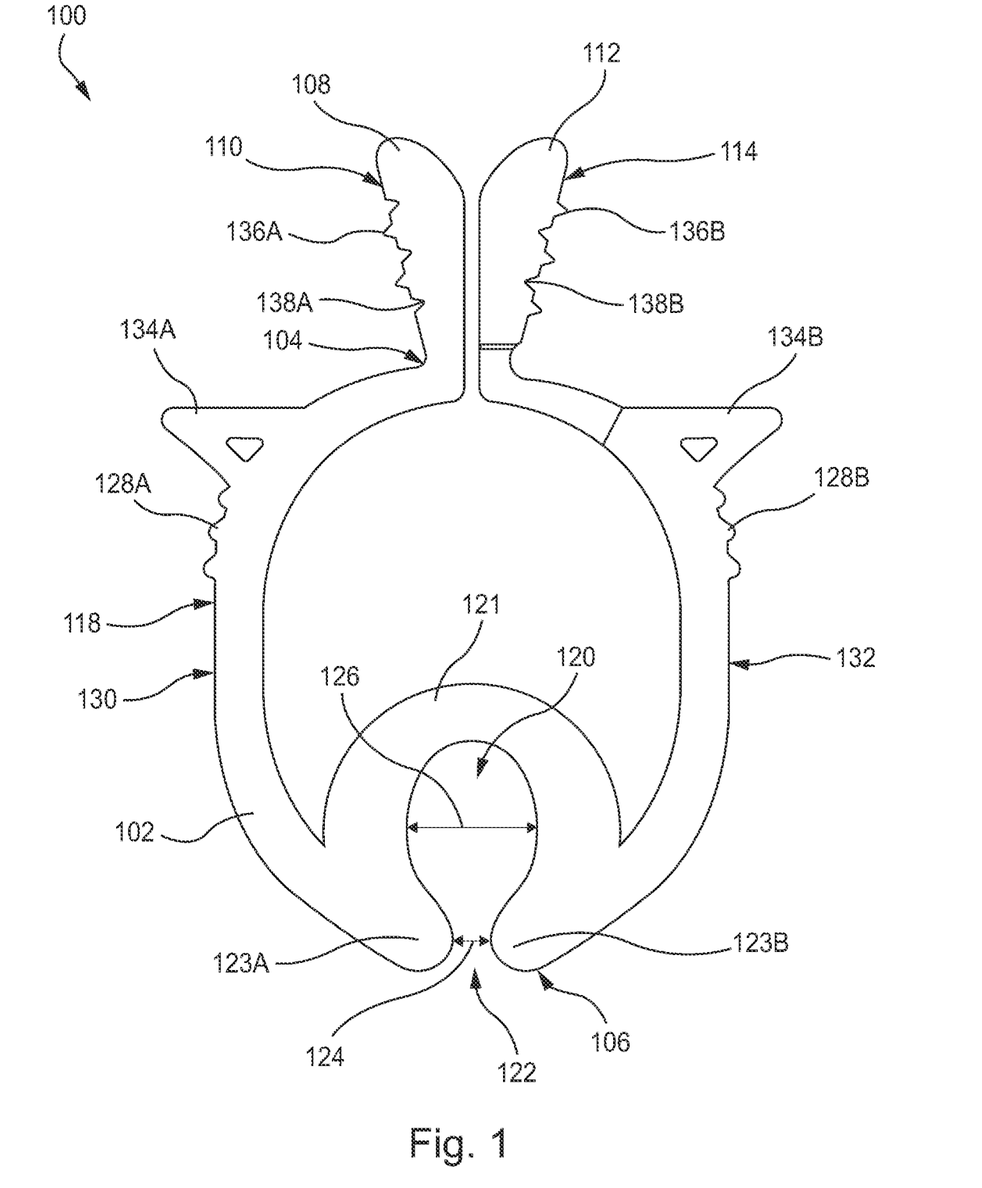
FIG. 1 illustrates a front view of an example device, according to an example embodiment.
Figure 4A:
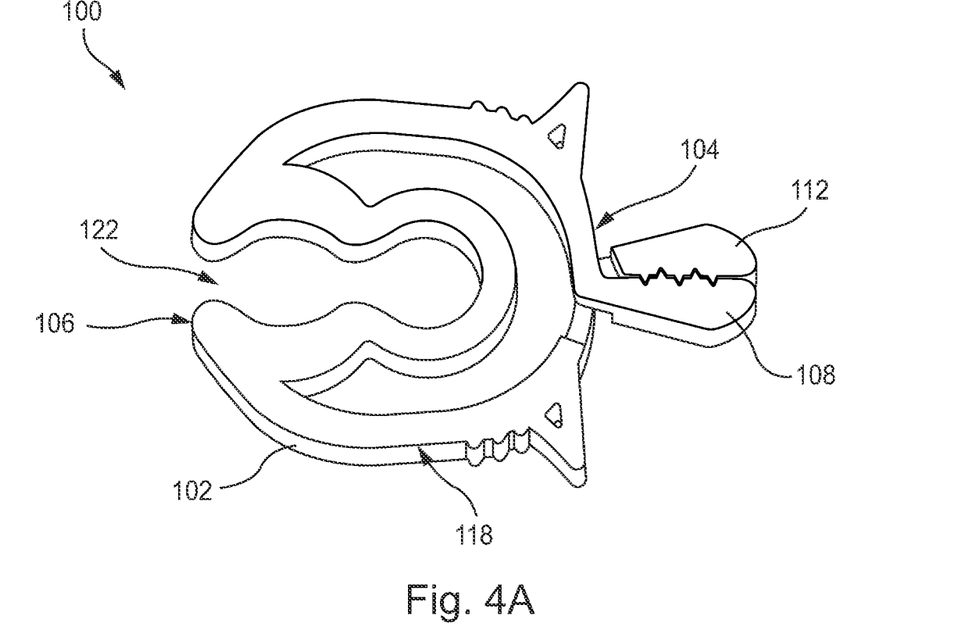
FIG. 4A illustrates a front view of the device of FIG. 2 in a first position, according to an example embodiment.

With reference to the Figures, FIG. 1 illustrates a device 100 for holding at least one conduit, according to an example embodiment. As shown in FIG. 1, the device 100 includes a ring 102 having a first end 104 and a second end 106. The ring may be a continuous ring or a split ring as illustrated in FIG. 1. The device 100 further includes a first clamping jaw 108 extending from the first end 104 of the ring 102. The first clamping jaw 108 includes a first clamping surface 110. The device 100 further includes a second clamping jaw 112 extending from the first end 104 of the ring 102. The second clamping jaw 112 includes a second clamping surface 114. The device 100 transitions from a first position, wherein the first clamping surface 110 contacts the second clamping surface (this is depicted in the embodiment of FIG. 4A) to a second position, wherein the first clamping surface 110 is spaced apart from the second clamping surface 114, in response to application of an external force applied to an exterior surface 118 of the ring 102 between the first end 104 and the second end 106. The first position may be a neutral position (e.g., a position where no external forces are applied to the device).

The device 100 further includes a channel wall 121 defining a channel 120 including an inlet 122 positioned at the second end 106 of the ring 102. The channel wall 121 includes opposing inlet wall portions 123A, 123B that define an inlet 122. The channel 120 is configured to releasably receive the at least one conduit via the inlet 122, and at least a portion of the channel wall 121 is positioned between the channel 120 and the first end 104 of the ring 102. The channel 120 may have a circular or elliptical cross-section, as non-limiting examples. In one example, each of the ring 102, the first clamping jaw 108, the second clamping jaw 112, and the channel wall 121 are formed as a single integral component fabricated of a polymeric material. The polymeric material may be a flexible material such that the device 100 may be manipulated to move the inlet wall portions 123A, 123B between an open position wherein the at least one conduit may be received into the channel 120 via the inlet 122, and a closed position wherein the opposing inlet wall portions 123A, 123B capture the at least one conduit in the channel. In another embodiment, the at least one conduit is flexible such that it can be pressed through, or narrowed such as by pinching to pass through, the inlet 122 to be secured in the channel 120.

In one example, as shown in FIG. 1, a width 124 of the inlet 122 is less than a maximum diameter 126 of the channel 120. Further, the width 124 of the inlet 122 may be less than a diameter of the at least one conduit that the device 100 is configured to hold. Such arrangements may help secure one or more conduits positioned therein once the conduits pass through the inlet 122 and are positioned in the channel 120. Both the width 124 of the inlet 122 and the maximum diameter 126 of the channel 120 may be determined based on the particular use case of the device 100. In one particular example, the maximum diameter 126 of the channel 120 ranges from about 0.20 in to about 0.40 in., and the width 124 of the inlet 122 ranges from about 0.15 in. to about 0.25 in.

In another example, as shown in FIG. 1, the device 100 further includes a first plurality of protrusions 128A positioned on a first side 130 of the ring 102 between the first end 104 of the ring 102 and the second end 106 of the ring 102, and a second plurality of protrusions 128B positioned on a second side 132 of the ring 102 between the first end 104 of the ring 102 and the second end 106 of the ring 102. The first plurality of protrusions 128A and the second plurality of protrusions 128B may be semicircular cylinders, round protrusions, angular teeth, or other shapes. The first plurality of protrusions 128A and the second plurality of protrusions 128B provide a gripping surface for a user to apply an external force (such as external force 116 depicted in FIG. 4B) to the exterior surface 118 of the ring 102 to thereby transition the device 100 from the first position to the second position.

In another example, as shown in FIG. 1, the device 100 further includes a first finger wing 134A extending from the first side 130 of the ring 102 between the first plurality of protrusions 128A and the first end 104 of the ring 102, and a second finger wing 134B extending from the second side 132 of the ring 102 between the second plurality of protrusions 128B and the first end 104 of the ring 102. In one example, the first finger wing 134A and the second finger wing 134B comprise triangular shaped projections extending from the first and second sides 130, 132 of the ring 102, respectively. Other shapes are possible as well. The first finger wing 134A and the second finger wing 134B may provide improved leverage for the user and may help prevent a user's fingers from sliding along the exterior surface 118 when applying the external force 116 to the exterior surface 118 of the ring 102 to thereby transition the device 100 from the first position to the second position.

As shown in FIG. 1, the device 100 may further include a first plurality of teeth 136A extending from the first clamping surface 110 of the first clamping jaw 108 and a second plurality of teeth 136B extending from the second clamping surface 114 of the second clamping jaw 112. In one example, the first plurality of teeth 136A and the second plurality of teeth 136B comprise triangular shaped projections extending from the first and second clamping surfaces 110, 114. Other shapes are possible as well. Further, the device 100 may additionally include a first plurality of cavities 138A in the first clamping surface 110 of the first clamping jaw 108, and a second plurality of cavities 138B in the second clamping surface 114 of the second clamping jaw 112. The first plurality of cavities 138A are positioned to receive the second plurality of teeth 136B when the device 100 is in the first position, and the second plurality of cavities 138B are positioned to receive the first plurality of teeth 136A when the device 100 is in the first position. As such, the shape of the first plurality of cavities 138A and the second plurality of cavities 138B may be complementary to the first plurality of teeth 136A and the second plurality of teeth 136B. For example, first plurality of cavities 138A and the second plurality of cavities 138B may comprise triangular shaped cutouts in the first and second clamping surfaces 110, 114. In one particular example, the first plurality of teeth 136A comprises two teeth, the first plurality of cavities 138A comprises three cavities, the second plurality of teeth 136B comprises three teeth, and the second plurality of cavities 138B comprises two cavities. In another example, the first plurality of teeth 136A comprises three teeth, the first plurality of cavities 138A comprises two cavities, the second plurality of teeth 136B comprises two teeth, and the second plurality of cavities 138B comprises three cavities. Other quantities of teeth and cavities are possible as well.

The first plurality of teeth 136A and the second plurality of teeth 136B and/or the first plurality of cavities 138A and second plurality of cavities 138B provide an improved gripping strength to hold a material positioned between the first clamping jaw 108 and the second clamping jaw 112, and to prevent undesired pullout of the material from the first and second clamping jaws 108, 112. In one example, the device 100 is adapted to clip the at least one conduit to a bed sheet or to clothing. In such an example, the first plurality of teeth 136A and the second plurality of teeth 136B may be received by the first plurality of cavities 138A and second plurality of cavities 138B, respectively, with the bed sheet or clothing positioned between the first clamping jaw 108 and the second clamping jaw 112.

The device 100 enables a practitioner to be able to control the placement and positioning of these conduits so that the conduits do not interfere with other medical procedures or general patient movement. Further, to assist with such a goal, the first and second clamping jaws 108, 112 of the device 100 are easily securable to a stationary surface, such as a sheet material associated with the bed or patient. Traditionally, such conduit management and clamping functions were separated into two components. The device 100 described herein provides an integrated clip and conduit management device capable of being operated with one hand that allows for holding at least one conduit and further securing of the device to a sheet material. The combined sheet clip and conduit management device 100 described herein provides improved grip strength and ease of operation over previous devices, while reducing the amount of material required to manufacture the clip since the conduit management and clamping functions are integrated into a single device.

Figure 2:
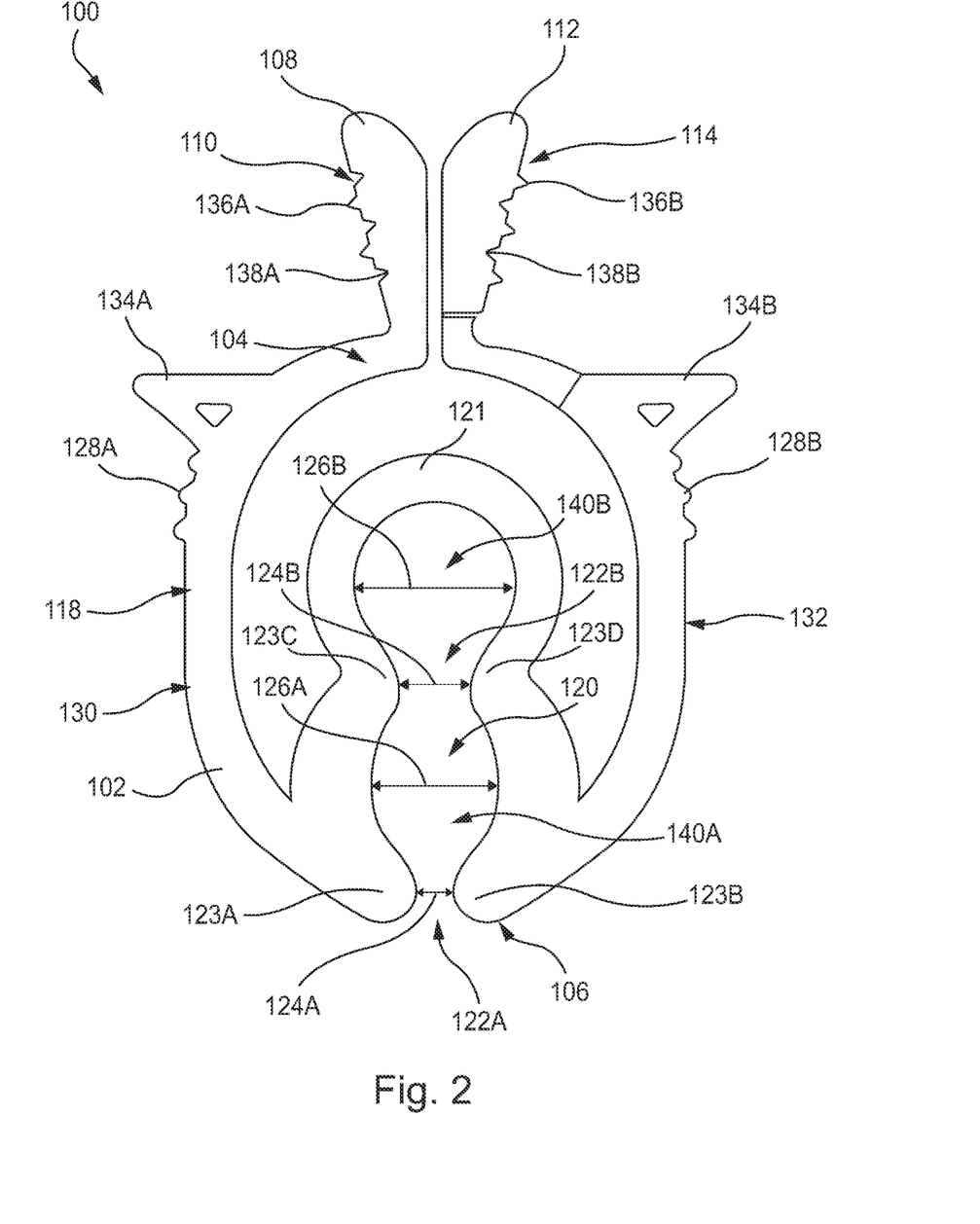
FIG. 2 illustrates a front view of another example device, according to an example embodiment.

FIG. 2 illustrates a front view of an example device, according to an example embodiment. In the example shown in FIG. 2, the inlet 122 of the channel 120 comprises a first inlet 122A, the channel 120 comprises a first lobe 140A having a first maximum diameter 126A, the channel 120 comprises a second lobe 140B having a second maximum diameter 126B, and the channel 120 further comprises a second inlet 122B defined by opposing inlet wall portions 123C, 123D of the channel wall 121, the second inlet 122B positioned between the first lobe 140A and the second lobe 140B. In one example, a width 124A of the first inlet 122A is equal to a width 124B of the second inlet 122B, and the first maximum diameter 126A is equal to the second maximum diameter 126B. In another example, the width 124A of the first inlet 122A is different than the width 124B of the second inlet 122B, and the first maximum diameter 126A is different than the second maximum diameter 126B.

The arrangement of FIG. 2 provides the ability to position a first conduit in the first lobe 140A and a second conduit in the second lobe 140B.

Figure 3:
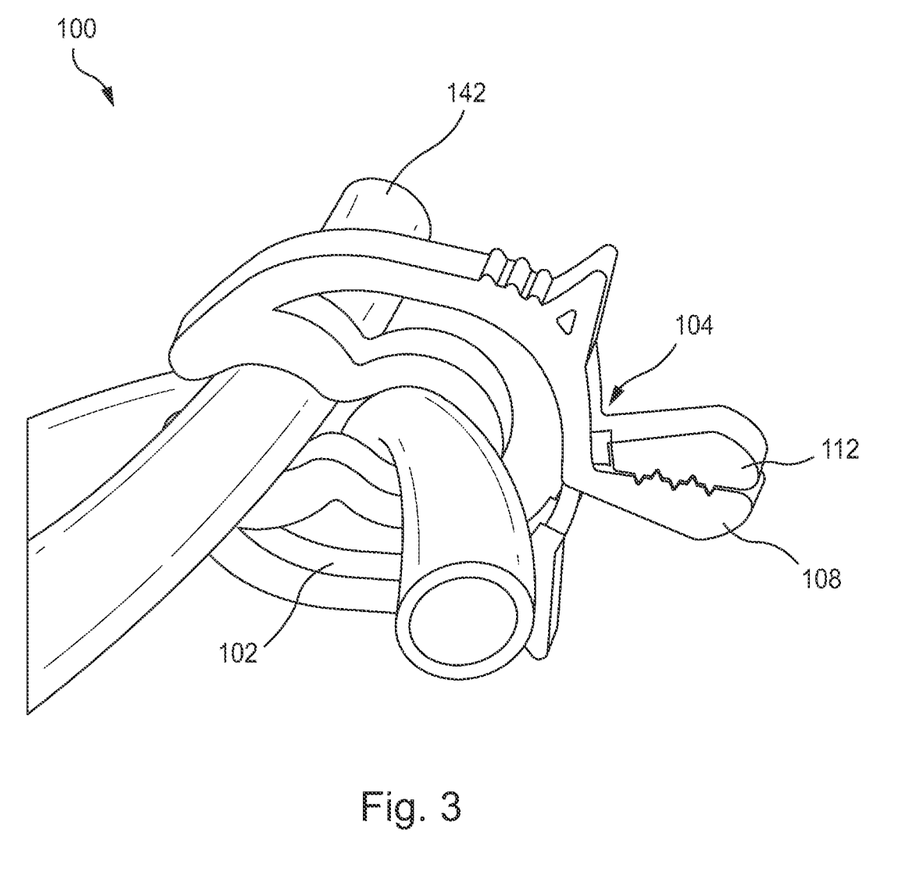
FIG. 3 illustrates a conduit positioned in the channel of the device of FIG. 2, according to an example embodiment.

FIG. 3 illustrates a conduit 142 positioned in the channel 120 of the device 100 of FIG. 2, according to an example embodiment. The example depicted in FIG. 3 shows how such an arrangement provides the ability to position a first portion of the conduit 142 through the first inlet 122A, through the second inlet 122B, and into the first lobe 140A of the channel 120, and position a second portion of the conduit 142 through the first inlet 122A and into the second lobe 140B of the channel 120.

FIG. 4A illustrates a front view of the device 100 of FIG. 2 in a first position, according to an example embodiment. While FIG. 4A shows the embodiment of FIG. 2, a similar arrangement would correspond to the device 100 of FIG. 1 (e.g., an embodiment with a single lobe in the channel 120). As shown in FIG. 4A, when in use, the first clamping surface 110 contacts the second clamping surface 114 in the first position. The first position may be a neutral position (e.g., a position where no external forces are applied to the device).

Figure 4B:
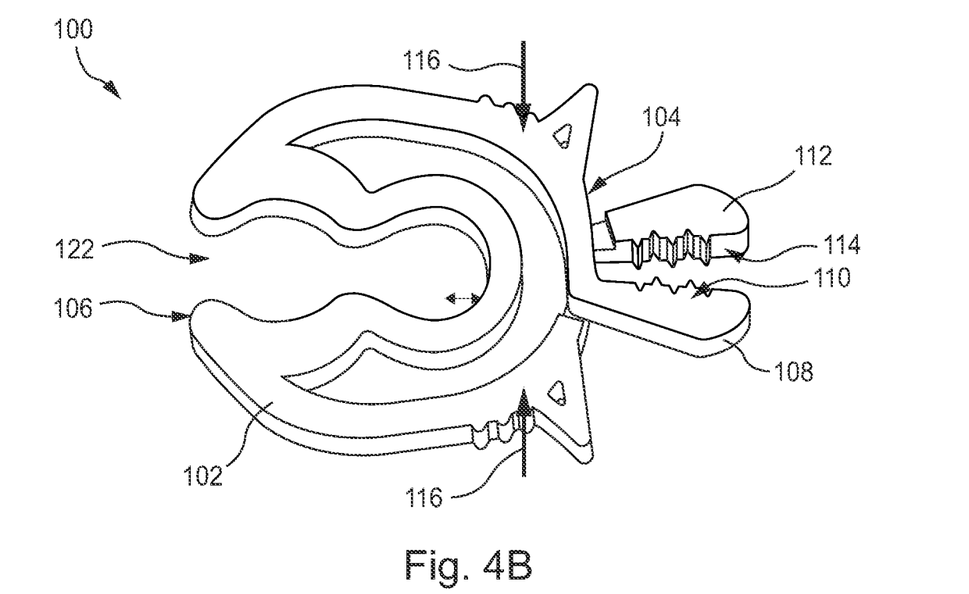
FIG. 4B illustrates a front view of the example device of FIG. 4A in a second position, according to an example embodiment.

FIG. 4B illustrates a front view of the example device 100 of FIG. 4A in a second position, according to an example embodiment. The device 100 transitions from the first position to a second position, in which the first clamping surface 110 is spaced apart from the second clamping surface 114, in response to application of an external force 116 applied to an exterior surface 118 of the ring 102 between the first end 104 and the second end 106. The external force 116 may be a pinching of the fingers of the user on either side 130, 132 of the ring 102. Other external forces are possible as well.

In use, a user may provide an external force 116 to the exterior surface 118 of the ring 102 to thereby transition the device 100 from the first position to the second position. The device 100 may be configured to withstand a maximum load ranging from about 1.5 lbf to about 4 lbf. The external force 116 may both increase the distance between the first clamping jaw 108 and the second clamping jaw 112, and simultaneously increase the width 124 of the inlet 122 of the channel 120 from a first width to a second width. The increased distance between the first clamping jaw 108 and the second clamping jaw 112 enables the user to remove or place a sheet material between the first and second clamping jaws 108, 112. The increased width 124 of the inlet 122 of the channel 120 when the user provides the external force 116 may help assist the user in positioning the at least one conduit in the channel 120. The channel 120 may provide a frictional fit with the at least one conduit. As discussed above, the at least one conduit may comprise any tubing or conduit consisting of a long object (usually cylindrical) used to hold and/or conduct objects, liquids, gases, electrical current, cabling, or transmit data appropriate for use in the medical field. In one particular example, the at least one conduit comprises urology tubing, although other conduits are possible as well.

Figure 5:
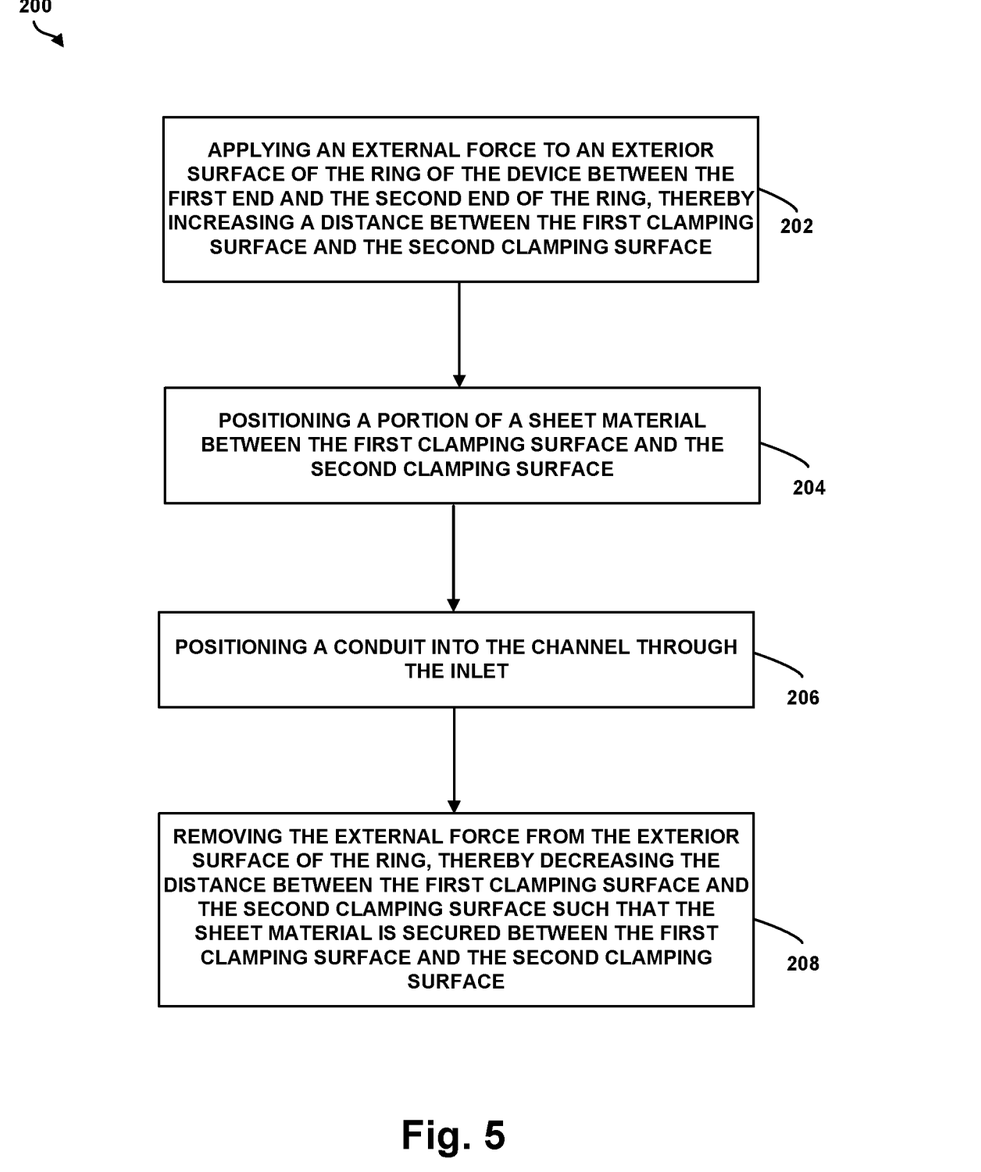
FIG. 5 is a flow chart depicting functions that can be carried out in accordance with example embodiments of the disclosed methods.

FIG. 5 is a simplified flow chart illustrating a method 200 according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 202, the method 200 includes applying an external force 116 to an exterior surface 118 of the ring 102 of the device described above in relation to FIGS. 1-4 between the first end 104 and the second end 106 of the ring 102, thereby increasing a distance between the first clamping surface 110 and the second clamping surface 114. In one example, applying the external force 116 to the exterior surface 118 of the ring 102 also increases a width 124 of the inlet 122 of the channel 120 from a first width to a second width. At block 204, the method 200 includes positioning a portion of a sheet material between the first clamping surface 110 and the second clamping surface 114. The sheet material may comprise a bed sheet, a blanket, or clothing of a patient, as non-limiting examples. At block 206, the method 200 includes positioning a conduit into the channel 120 through the inlet 122. At block 208, the method includes removing the external force 116 from the exterior surface 118 of the ring 102, thereby decreasing the distance between the first clamping surface 110 and the second clamping surface 114 such that the sheet material is secured between the first clamping surface 110 and the second clamping surface 114.

As discussed above in relation to FIG. 3, in one example the inlet 122 of the channel 120 comprises a first inlet 122A, the channel 120 comprises a first lobe 140A having a first maximum diameter 126A, the channel 120 comprises a second lobe 140B having a second maximum diameter 126B, and the channel 120 comprises a second inlet 122B positioned between the first lobe 140A and the second lobe 140B. In such an example, the method 200 may further include (i) positioning a first portion of the conduit through the first inlet 122A, through the second inlet 122B, and into the first lobe 140A of the channel 120, and (ii) positioning a second portion of the conduit through the first inlet 122A and into the second lobe 140B of the channel 120. In another example, the method may further include (i) positioning a first conduit through the first inlet 122A, through the second inlet 122B, and into the first lobe 140A of the channel 120, and (ii) positioning a second conduit through the first inlet 122A and into the second lobe 140B of the channel 120.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

What is claimed is:

1. A device for holding at least one conduit, the device comprising:
   a ring having a first end and a second end;
   a first clamping jaw extending from the first end of the ring, wherein the first clamping jaw includes a first clamping surface;
   a second clamping jaw extending from the first end of the ring, wherein the second clamping jaw includes a second clamping surface, wherein the first clamping surface contacts the second clamping surface in a first position, wherein the first clamping surface is spaced apart from the second clamping surface in a second position, wherein the device transitions from the first position to the second position in response to application of an external force applied to an exterior surface of the ring between the first end and the second end; and
   a channel including an inlet positioned at the second end of the ring, wherein the channel is configured to releasably receive the at least one conduit via the inlet, and wherein the channel prevents the at least one conduit from contacting the first end of the ring, wherein the channel includes a channel wall and at least a portion of the channel wall is positioned between the channel and the first end of the ring, such that the at least one conduit is received within an inner perimeter of the ring.

2. The device of claim 1, wherein a width of the inlet of the channel is less than a maximum diameter of the channel.

3. The device of claim 2, wherein the maximum diameter of the channel ranges from about 0.20 in to about 0.40 in., and wherein the width of the inlet ranges from about 0.15 in. to about 0.25 in.

4. The device of claim 1, wherein the inlet of the channel comprises a first inlet, wherein the channel comprises a first lobe having a first maximum diameter, wherein the channel comprises a second lobe having a second maximum diameter, and wherein the channel comprises a second inlet positioned between the first lobe and the second lobe.

5. The device of claim 4, wherein a width of the first inlet is equal to a width of the second inlet, and wherein the first maximum diameter is equal to the second maximum diameter.

6. The device of claim 4, wherein a width of the first inlet is different than a width of the second inlet, and wherein the first maximum diameter is different than the second maximum diameter.

7. The device of claim 1, further comprising:
   a first plurality of protrusions positioned on a first side of the ring between the first end of the ring and the second end of the ring; and
   a second plurality of protrusions positioned on a second side of the ring between the first end of the ring and the second end of the ring, wherein the first plurality of protrusions and the second plurality of protrusions provide a gripping surface for a user to transition the device from the first position to the second position.

8. The device of claim 7, further comprising:
   a first finger wing extending from the first side of the ring between the first plurality of protrusions and the first end of the ring; and
   a second finger wing extending from the second side of the ring between the second plurality of protrusions and the first end of the ring, wherein the first finger wing and the second finger wing provide improved leverage for the user to transition the device from the first position to the second position.

9. The device of claim 1, further comprising:
a first plurality of teeth extending from the first clamping surface of the first clamping jaw; and
a second plurality of teeth extending from the second clamping surface of the second clamping jaw.

10. The device of claim 9, further comprising:
a first plurality of cavities in the first clamping surface of the first clamping jaw, wherein the first plurality of cavities are positioned to receive the second plurality of teeth when the device is in the first position; and
a second plurality of cavities in the second clamping surface of the second clamping jaw, wherein the second plurality of cavities are positioned to receive the first plurality of teeth when the device is in the first position.

11. The device of claim 10, wherein the first plurality of teeth comprises two teeth, wherein the first plurality of cavities comprises three cavities, wherein the second plurality of teeth comprises three teeth, and wherein the second plurality of cavities comprises two cavities.

12. The device of claim 1, wherein a width of the inlet of the channel increases from a first width to a second width as the device transitions from the first position to the second position.

13. The device of claim 1, wherein the device is adapted to clip the at least one conduit to a sheet or to clothing.

14. The device of claim 1, wherein the channel has a circular or elliptical cross-section.

15. The device of claim 1, wherein each of the ring, the first clamping jaw, the second clamping jaw, and the channel are formed as a single integral component fabricated of a polymeric material.

16. The device of claim 1, wherein the at least one conduit comprises medical tubing or electrical cords.

17. The device of claim 1, wherein the channel provides a frictional fit with the at least one conduit.

18. A device for holding at least one conduit, the device comprising:
a ring having a first end and a second end;
a first clamping jaw extending from the first end of the ring, wherein the first clamping jaw includes a first clamping surface;
a second clamping jaw extending from the first end of the ring, wherein the second clamping jaw includes a second clamping surface, wherein the first clamping surface contacts the second clamping surface in a first position, wherein the first clamping surface is spaced apart from the second clamping surface in a second position, wherein the device transitions from the first position to the second position in response to application of an external force applied to an exterior surface of the ring between the first end and the second end; and
a channel including an inlet positioned at the second end of the ring, wherein the channel is configured to releasably receive the at least one conduit via the inlet, and wherein the channel prevents the at least one conduit from contacting the first end of the ring, and wherein the channel includes a channel wall movable between an open position and a closed position.

19. The device of claim 18, wherein at least one conduit may be received into the channel via the inlet when channel wall is in the open position.

20. The device of claim 18, wherein the channel wall may capture the at least one conduit in the channel when the channel wall is in the closed position.

* * * * *